(12) United States Patent
Trautwein et al.

(10) Patent No.: US 9,452,064 B2
(45) Date of Patent: Sep. 27, 2016

(54) INTERVERTEBRAL MEDICAL IMPLANT

(75) Inventors: Frank Trautwein, Filderstadt (DE); Frank Heuer, Filderstadt (DE); Jorg Franke, Magdeburg (DE); Ralph Kothe, Herdecke (DE); Ulf Liljenqvist, Munster (DE); Guy Matge, Mamer (LU); Michael Putzier, Stahnsdorf (DE)

(73) Assignee: ACES INGENIEURGESELLSCHAFT MBH, Filderstadt (DE)

( * ) Notice: Subject to any disclaimer, the term of this patent is extended or adjusted under 35 U.S.C. 154(b) by 477 days.

(21) Appl. No.: 13/877,851

(22) PCT Filed: Oct. 5, 2011

(86) PCT No.: PCT/DE2011/050040
§ 371 (c)(1),
(2), (4) Date: Jun. 27, 2013

(87) PCT Pub. No.: WO2012/052006
PCT Pub. Date: Apr. 26, 2012

(65) Prior Publication Data
US 2013/0304211 A1 Nov. 14, 2013

(30) Foreign Application Priority Data
Oct. 5, 2010 (DE) .................. 10 2010 041 959

(51) Int. Cl.
*A61F 2/44* (2006.01)
*A61L 27/04* (2006.01)
(Continued)

(52) U.S. Cl.
CPC ............ *A61F 2/447* (2013.01); *A61F 2/442* (2013.01); *A61F 2/4455* (2013.01); *A61L 27/04* (2013.01); *A61L 27/14* (2013.01); *A61F 2/30942* (2013.01);
(Continued)

(58) Field of Classification Search
CPC .. A61F 2/44; A61F 2/442; A61F 2002/4435; A61F 2/4455; A61F 2/447
USPC .................... 606/246–249; 623/17.11–17.16
See application file for complete search history.

(56) References Cited

U.S. PATENT DOCUMENTS

| 5,108,432 A | 4/1992 | Gustavson |
| 5,732,469 A | 3/1998 | Hamamoto et al. |

(Continued)

FOREIGN PATENT DOCUMENTS

| WO | WO0224122 | 3/2002 |
| WO | WO02071921 | 9/2002 |
| WO | WO2006091097 | 8/2006 |

*Primary Examiner* — Ellen C Hammond
*Assistant Examiner* — Christina Negrellirodrigue
(74) *Attorney, Agent, or Firm* — Hoffmann & Baron, LLP (57) ABSTRACT

The invention relates to a spinal implant composed of a plurality of parallel plates. The deliberate introduction of contours in the plates allows for the creation of biomechanically advantageous functions and adjustment options. The elasticity of the anchoring elements enables the disclosed implant to be adjusted to the osseous endplates, resulting in uniform force distribution and thus prevention of the risk of compaction or endplate compression fracture. The plate structure allows for the use of production methods in which hook-like undercut contours can be created, thus enabling the implant to be superbly anchored in the bone without causing damage thereto. Furthermore, the plates can be interconnected by an actuator in such a way that the height and/or the angular position can be adjusted. The vertical adjustment can vary along the length of the implant such that the segment can also be angularly adjusted.

23 Claims, 12 Drawing Sheets

(51) Int. Cl.
*A61L 27/14* (2006.01)
*A61F 2/30* (2006.01)
*A61F 2/48* (2006.01)

(52) U.S. Cl.
CPC *A61F 2002/3092* (2013.01); *A61F 2002/3093* (2013.01); *A61F 2002/3097* (2013.01); *A61F 2002/30322* (2013.01); *A61F 2002/30433* (2013.01); *A61F 2002/30472* (2013.01); *A61F 2002/30517* (2013.01); *A61F 2002/30553* (2013.01); *A61F 2002/30556* (2013.01); *A61F 2002/30563* (2013.01); *A61F 2002/30576* (2013.01); *A61F 2002/30579* (2013.01); *A61F 2002/30593* (2013.01); *A61F 2002/30596* (2013.01); *A61F 2002/30598* (2013.01); *A61F 2002/30601* (2013.01); *A61F 2002/30604* (2013.01); *A61F 2002/30616* (2013.01); *A61F 2002/30622* (2013.01); *A61F 2002/30668* (2013.01); *A61F 2002/30736* (2013.01); *A61F 2002/30784* (2013.01); *A61F 2002/30892* (2013.01); *A61F 2002/30904* (2013.01); *A61F 2002/30925* (2013.01); *A61F 2002/30971* (2013.01); *A61F 2002/30976* (2013.01); *A61F 2002/30978* (2013.01); *A61F 2002/448* (2013.01); *A61F 2002/4475* (2013.01); *A61F 2002/482* (2013.01); *A61L 2430/38* (2013.01)

(56) References Cited

U.S. PATENT DOCUMENTS

| | | | |
|---|---|---|---|
| 6,200,347 B1 * | 3/2001 | Anderson | A61F 2/28 623/11.11 |
| 6,595,998 B2 * | 7/2003 | Johnson | A61B 17/025 606/247 |
| 6,761,738 B1 * | 7/2004 | Boyd | 623/17.11 |
| 2005/0112397 A1 | 5/2005 | Rolfe et al. | |
| 2006/0224241 A1 * | 10/2006 | Butler | A61B 17/8858 623/17.15 |
| 2010/0075419 A1 | 3/2010 | Inagaki et al. | |

* cited by examiner

INTERVERTEBRAL MEDICAL IMPLANT

TECHNICAL FIELD

The invention relates to a medical implant that can be inserted in the intervertebral space of two vertebrae to stabilize the spine. The implant according to the invention is essentially characterized by the fact that the implant is composed of a plurality of thin plates, thereby allowing for achieving further advantageous properties regarding manufacture, implantation and function inside the body.

PRIOR ART

In diseases of the spine, it is often necessary to stabilize one or several spine segments. A plurality of intervertebral transplants (also referred to as "cages") is available for this purpose having the goal of creating a bony fusion of a section of the spine. The implantation of such cages can be associated with numerous complications. For example, endplate compression fractures can occur due to the localized stress application or the small placement area of the implant, the desired bony fusion can be unsuccessful due to stress shielding, the implants can slip out of place, or the position of the vertebral bodies relative to each other cannot be sufficiently corrected. Moreover, a secondary support function (for example, by means of a pedicle-screw-and-rod system) is typically needed to stabilize the segment insofar that any migration of these implants is reliably prevented.

(WO 9501763A1 1993) discloses a spinal implant made of a basket-type ring with a central opening for receiving the bone material. (EP1800627A2 2005) specifies that, for an enlargement of the contact areas, a spine implant system can be made of two or a plurality of rings to reduce the occurrence of compression fractures of the vertebral endplates. (WO 0234171A2 2000) discloses deformable polymer strips that are inserted in the intervertebral space and can be aligned relative to the load direction.

Applications (U.S. Pat. No. 6,767,738B1 2004) and (WO 2008079953A2 2006), respectively, propose an apparatus of two or three rigidly connected plates that, owing to the plate distances, allow for a space suitable for importing bone graft material, bone substitute graft material or bone morphogenetic protein (BMP). In this case, the plates have the function of a receptacle for importing the mechanically unstable bone graft material into the intervertebral space and preventing any undesired distribution in the vertebral disc space and/or the body. Due to the desired function and the small number of plates, no workable preparations are envisioned for determining the clearances between of a larger number of plates. It is also disadvantageous that the bone graft material for filling the space must be harvested and/or other bone substitute graft materials must be provided and imported.

(WO 0045747A1 1998) and (WO0040177A1 1999) teach layered apparatuses comprised of bone graft materials.

The previous inventions that have been referred to above are comprised of or allow for importing bone graft or bone graft substitute materials into the intervertebral space; however, they are unable to correct a misaligned vertebral position (angle and offset), nor do they offer solutions for achieving an even load distribution on the endplates of the vertebral bodies. Due to the fact that the height of the implants is not adjustable, in part high placement forces and (over)distraction of the endplates is required during implantation.

(WO 0044319A1 1999) discloses an expandable spine implant. Numerous folded elements can be inserted through a small intervertebral disc access and set up such by means of a compression thereof that they distract the vertebrae. Further, (DE 19816832C1 1998) and (US 2010010633A1 2008) teach spine implants that possess at least one shaft with discs that are eccentrically mounted thereto. The shaft can be rotated such that the discs are extended and the construction height of the implant increases. A potential disadvantage of this embodiment is the need for a rigid connection between the shaft and the discs. These spine implants are moreover restricted to distraction applications, wherein displacement of the vertebrae relative to each other cannot be completely precluded from occurring, due to the rotatable shaft and the resulting friction between the discs and the endplates. Clinical experience has shown that, due to the for the most part cylindrical cross-section, a plurality of these implants cause compression fractures of the endplate and that these are in part only difficult to resolve.

(US 2010016968A1 2007) and (WO 2007048012A2 2005) disclose methods and implants for repositioning a slipped vertebra. To this end, two implanted halves are shifted relative to each other until reaching the end position. The attachments herein are based on temporarily implanted instruments that must be removed again after the final treatment.

Aside from the various previously described inadequacies, none of the implants known to date contain any teeth or, if they do, only simple teeth on the bone-contact surfaces to increase the resistance against migration. Any mechanical generation of defined tooth geometries including an undercut has been unknown in the art, due to the construction and manufacturing types that have been used to date. When bone graft material is used as an implant material, the low level of solidity of these materials precludes any configuration and application of toothed geometries of this kind.

DESCRIPTION OF THE INVENTION

Technical Object

The object of the present invention envisions providing an implant for stabilizing the spine via the intervertebral space. Important tasks of the implant according to the invention include an even load distribution over a contact area that is as large as possible, as well as simple yet secure anchoring in the contact surfaces without causing mechanical weakening. Further optional embodiments allow for adding growth stimuli to the bone tissue by way of micro-movements of the implant structure, in situ adjustment of height and angle of the implant, as well as a correction of translational shifts and an omission of the requirement for filling the implant with bone graft or bone graft substitute materials. In addition, the implant according to the invention should also be cheap in terms of production and simplify any intra-operative handling thereof.

Technical Solution

The object is achieved by providing that the spine implant is made up of a plurality of plates that are essentially disposed in a parallel manner in one or two planes. On the side of the bone, the plates can have a filigree profile, wherein undercuts in the toothing structure allow for increasing the solidity of the anchoring action in the endplates even further. By the targeted application of further contours and/or structures on and/or in the plates it is possible to generate different, optional functions of the implant and combine the same with each other. For example, certain plate regions can have an elastic property and thereby adjust themselves to the endplate contour, and/or thereby counteract stress shielding. The rigidity can, furthermore, be adjusted such that it corresponds to that of bones, and whereby a stretch stimulus is sent to the surrounding tissue. In combination, the plates can be embodied with an actuator having an adjustment mechanism that can be implemented, for example, by an eccentric shaft, a mechanical, electrical or by a mechanism based on shape-memory properties and connected with the ability to execute relative movements in order to, for example, distract the intervertebral disc compartment or reset two vertebrae relative to each other.

Only the use of plates with thin wall strengths that are arranged in a parallel fashion allows for the low-cost manufacturing of the necessary, in part complex structures. The contours therein can be preferably produced by a photo-chemical etching process or cut out of the plates by means of energy-rich radiation (for example, laser, electron beams) and/or a water jet. Moreover, the contours can be produced, completely or partially, by wire erosion or injection molding (from metal or plastic materials).

Advantageous Effects

Advantageously, owing to the special toothing structure, the implant according to the invention offers very high resistance against migration and compression fractures of the base- and endplates. This creates a very high level of primary stability, thereby rendering any additional stabilization via ventral plates or dorsal rod systems superfluous in some patients. Due to the plurality of the resulting channels and/or lattice structures and an elastic support of the teeth and/or adjustment of the rigidity of the implant by means of expedient cut-outs, a great stimulus is moreover created for the formation of new bone tissue, specifically without the need of having to fill the implant with additional bone graft or bone graft substitute material. Due to the various adjustment possibilities, it is possible to achieve, on the one hand, optimal adjustment of the device to the patient's anatomy and, on the other hand, a simplification of the implant in embodiments that are distracted or can be angularly adjusted after the placement of the implant. A further variant also introduces a simple correction possibility with regard to the AP alignment of the vertebral bodies by means of a functionality that is integrated in the implant.

BRIEF DESCRIPTION OF THE DRAWINGS

FIG. 16 illustrates the work steps that must be taken into account when implementing the embodied example as previously referred to.

WAY(S) TO IMPLEMENT THE INVENTION

The technical solutions are described below, illustrated often in an exemplary manner. The comments below must be understood as an explanation of the underlying idea, not limited to each concrete representation. The embodied examples that are presently described in detail constitute a combination basis for the invention, meaning the embodied examples can be implemented separately or in combination.

Figure 1:
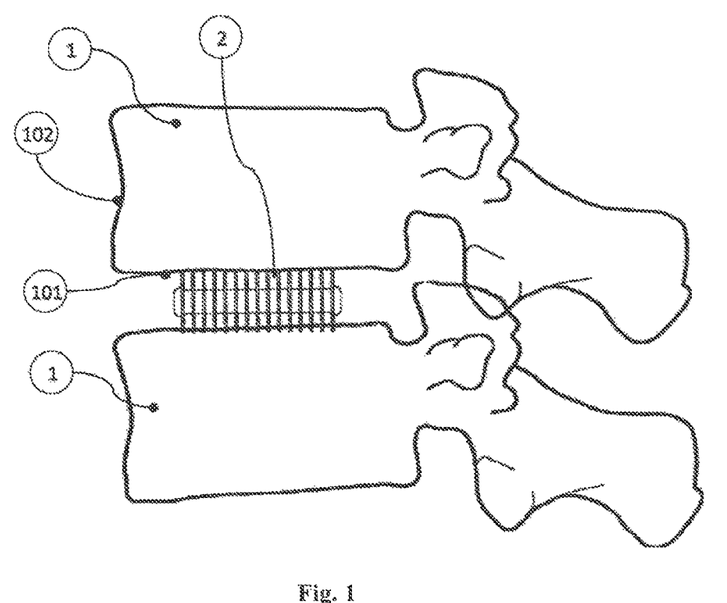
FIG. 1 shows the implantable invention for the fixation of a vertebra.
Figure 2:
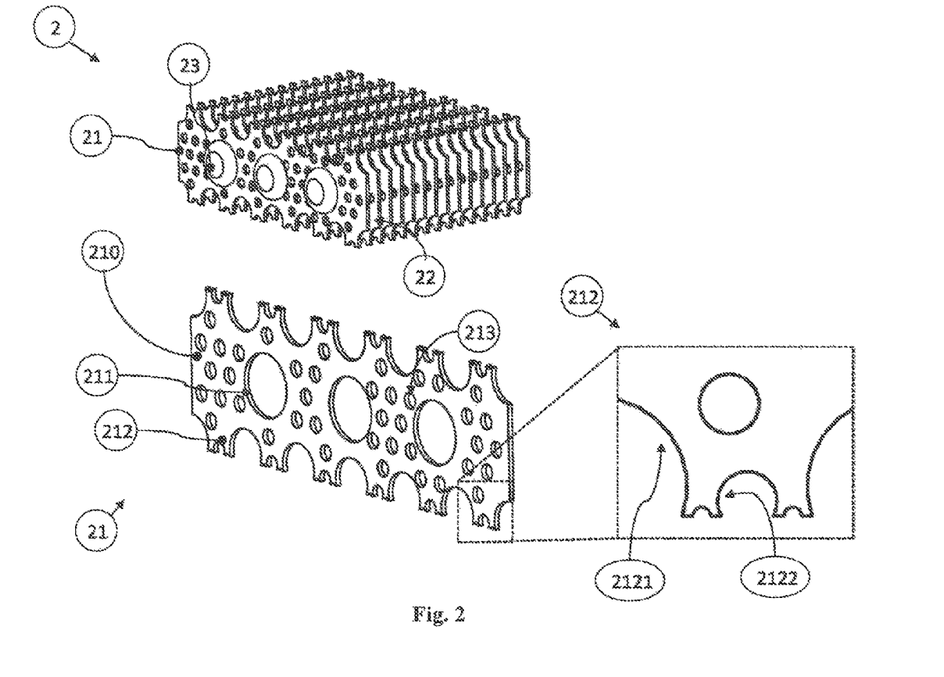
FIG. 2 describes the first embodied variant of the invention.

The implant according to the invention (2) is inserted in the intervertebral space of two vertebrae (1) in order to stabilize the spine (FIG. 1). At least one contact surface is created therein between the implant and the endplates (101) of the adjacent vertebrae (1). The spine implant (2) comprises a plurality of plates (21) that are connected, together with their clearances (22), utilizing the aid of at least one connection element (23) (FIG. 2). The plates (21, 210) have a wall thickness of 0.05 to 3 mm, particularly between 0.2 to 1.5 mm. The width of the clearances (22) is oriented on the size of the trabecular structure of the bone and is also between 0.05 and 3 mm, particularly between 0.2 and 1.5 mm. To configure capillaries and/or to improve solidity, the plates can also be disposed without clearance. If corresponding cut-outs (213) and/or the configuration of channels functioning as capillaries allows for achieving bone integration, it is possible, in this special case, to forego providing a clearance (distance=0 mm).

The plates can be manufactured, for example, by means of an injection molding process, from a metal (metal injection molding), plastic or another biocompatible and/or other bio-resorbable material, or from a combination of said materials. Other especially expedient manufacturing processes for the production of the plates are cutting processes with the aid of energy-rich radiation (electron beam, laser beam, water jet) or etching by means of a photo-chemical etching process from metal band, sheet metal or plates (photo-etching). The mentioned production processes offer a plurality of design possibilities for the plates and allow for a low-cost integration of functions into the implant that cannot be implemented by the known one- or two-part, essentially monolithic embodied examples. For example, it is easily possible to integrate structures, profiles, guide means, openings or toothed structures (212) of varying depths into the plates, to produce toothed structures with undercuts or dispose teeth respectively offset relative to the next plate. Correspondingly, the bone contact surface is able to provide, for example by a plurality of small branch-offs (2121), for a so-called micro-penetration of the endplate (101), wherein the branch-offs can be undercut (2122), thereby allowing for primarily stable anchoring stability of the bone already after a very short healing time, and whereby the solidity of the anchoring connection is clearly increased, particularly when subject to tensile stresses. Owing to the plate setup and the related possible manufacturing processes, it is possible to produce semi-permeable pores, capillaries or openings (213) that trigger the development of osmotic pressure on the inside of the implant, and whereby this osmotic pressure can be utilized in turn to support metabolism and cell differentiation. To configure the plate surface in an osteoconductive or/and osteoinductive manner, it is possible to provide the plates with a suitable material coating, or manufacture the same having a defined roughness. In addition, the material of all or of individual plates can be selected such that the same are resorbable over time. For a defined resorption over a long period of time, it makes sense to produce the plates having varying thicknesses and/or being made of varying materials with different resorption rates.

Figure 3:
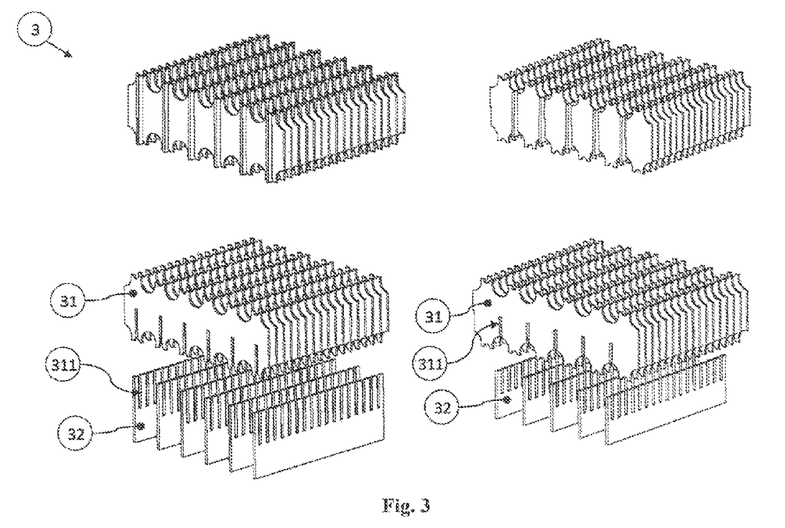
FIG. 3 describes a second embodied variant according to the invention with plates that can be plugged into each other.

In a further embodied variant (3), the plates can be configured such that they can be plugged into one another (FIG. 3). This can be achieved in that the plates (31) and/or (32) include slot-type connection openings (311) that are compatible with each other, respectively, and allow for the possibility of a positive connection. The distance of the slots (311) in the connection plate (32) defines therein the division and the distance of the clearance (22).

Figure 4:
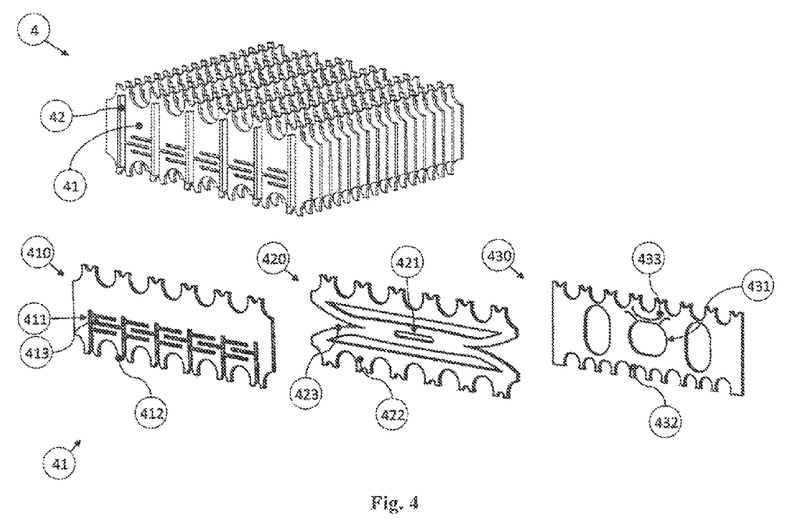
FIG. 4 shows the implementation of the anchoring elements for an even load distribution of the plates.

In a third embodied example of the invention (4), the dynamic configuration of the plates (41) in FIG. 4 is shown in an exemplary manner. This is why the implant is able to adjust itself to the endplate contour (101), thereby allowing for an even force distribution on the endplate without provoking an endplate compression fracture due to localized force and tension concentrations. The plates (410) therein can be configured such that each individual hook and tooth structure (412), constituting the bone contact surface, is supported in a spring-type fashion, for example, by means of a meandering-type contour section (413).

A further embodied variant is shown in FIG. 4 (420). Shown herein is how the spring-type support of the bone contact surface is made possible by more than one hook element (422) in that the contour cut-out (423) is configured as larger. Furthermore, the spring-type supported connection of the plates (430) can be used to achieve elasticity or a reduction in the rigidity of the totality of the implant. This can be achieved in that the connection openings (431) are provided with an adjacent contour cut-out (433) that allows for elastic pliability in the area of the load transfer surface of the connection and/or adjustment opening (431).

FIG. 4 shows, furthermore, different cut-out shapes (411, 421, 431) suited for receiving connection elements (42, 23, 5051, 5052, 5053, etc.) that are disposed for the most part in a perpendicular manner relative to the plates (41). The connection elements can be configured as a screw, pin, tube or axle having a round, oval, rectangular or polygonal cross-section. The connection elements in plate form (32, 42) are expedient for the targeted adjustment of a distance of the clearance (22) between the plates. The distance of the plates therein must preferably be selected in such a way that it is compatible with the structural size of the bone trabeculae, meaning ca. 0.02 to 3 mm and, in particular, between 0.2 and 1.5 mm. An alternate option for adjusting the distance of the clearance (22) is a graduation of the cross-section of the connection element (42, 5051, 5052, 5053, etc.) along the axis therein and of the connection opening (421, 431) of the plates (41). For a large number of plates, however, it is advantageous to use discs (5020, FIG. 10), rings or similar elements having a thickness that corresponds to the desired distance of the clearance (22). To this end, the spacers (5020) are disposed on the connection elements (23, 5051, 5052, 5053, etc.) between the plates (41), respectively. Finally, spatially offset embossing between the plates (41) is expedient for adjusting a defined distance (22) between the plates.

The implant can be designed such that the assembly of plates (21), connection element (23 and/or 32) and, if need be, separate spacer discs or rings (5020) occurs on a patient by patient basis during the surgery. This can be achieved by inserting an instrument in the intervertebral disc compartment that includes an adjustable or deformable area by means of which the endplate contour can be detected or temporarily copied. The instrument is later removed again from the intervertebral disc compartment, and the spine implant can thus be assembled during surgery using individual plates (21) of different height and width corresponding to the endplate contour.

Figure 5:
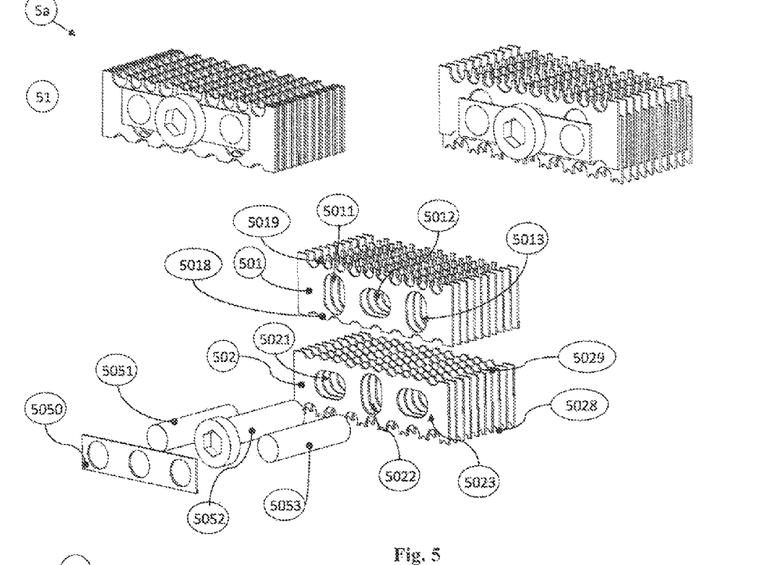
FIG. 5 illustrates the setup of a distractible implant.

A forth embodied variant (5a) introduces an implant according to the invention that has an adjustable height (FIG. 5). Upon inserting the spine implant (5a) in the intervertebral space, the combined plates, comprising upper (501) and lower (502) plates, initially have a minimum height, wherein the toothed structures (5019 and 5028) are covered up by flattened profiles (5018 and 5029), thereby allowing for easier insertion of the implant. Only after the height adjustment is complete, wherein the combined plates (501 and 502) are displaced relative to each other, do the toothed structures (5019 and 5028) protrude above the flattened profiles (5018, 5029) and into the endplates (101) serving as anchors therein. The plates (501 and 502) are configured such that they have diverse connection apertures. A distinction is made therein between the orientation of the openings for the supporting action (5011, 5013, 5021 and 5023) and the orientation of openings for achieving the relative movement (5012 and 5022) of the plates. The orientation of the openings (5011-5013) therein differs from the orientation of the openings (5021-5023) in order to achieve a relative movement between the combined plates (501 and 502), specifically rotated by 90° in a preferred embodiment. In this embodiment, the plates (501 and 502) are supported via two axes (5051 and 5053). The relative movement of the plates occurs by means of an actuator that is embodied, for example, by means of an eccentric shaft (5052) and an instrument connected thereto for the transfer of a rotary movement. A turning of the eccentric shaft (5052) causes cut-out (5012) and thereby the combined plates (501) to move analogously in relation to the position of the crank radius of the eccentric shaft (5052). A plate (5050) that is disposed vertically relative to the shaft or a frame that encloses the implant holds the connection elements (5051, 5053), the eccentric shaft (5052) and, indirectly via bearings (5051, 5053), the lower combined plates (502) in a constant position. The frame (5050) is not shown in further embodiments in order to open up the view onto the internal setup.

Figure 6:
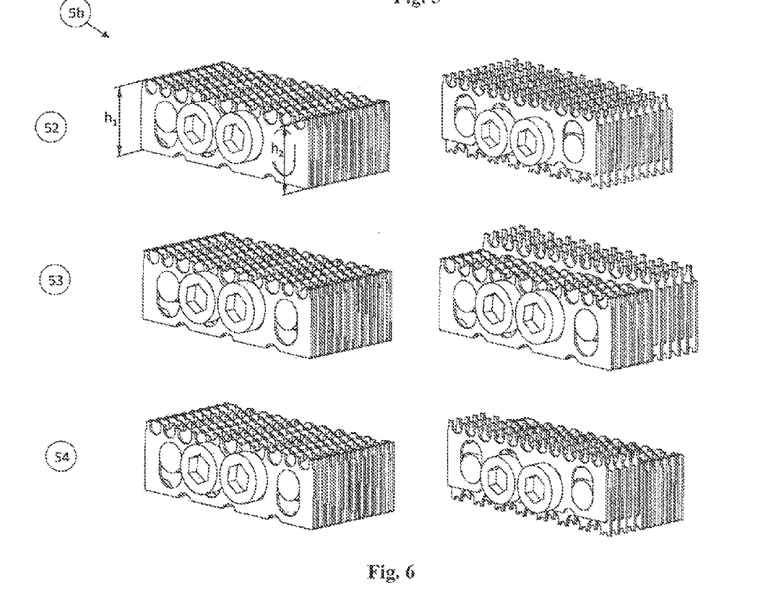
FIG. 6 explains a modification of the variant from FIG. 5.

Disadvantageously, in the variant according to FIG. 5, there exists a tilting tendency of the upper combined plates (501) over the eccentric shaft (5052). The embodied example (5a) can therefore be extended in such a way (FIG. 6, 5b) that two eccentric shafts (5052) are used. This is intended to prevent the tilting tendency of the combined plates and allows for the separate height adjustments h1 and h2. By configuring the cut-outs (5012) that influence the relative movements and/or the position and length of the section of the eccentricity on the eccentric shaft (5052), it is possible to adjust only parts of the respective combined plates. Correspondingly, it is possible, for example, that both regions (52) are varied in terms of the adjustment height thereof, meaning only the rear (53) or only the front region (54), when the eccentric shafts (5052, 5053) are rotated.

Figure 7:
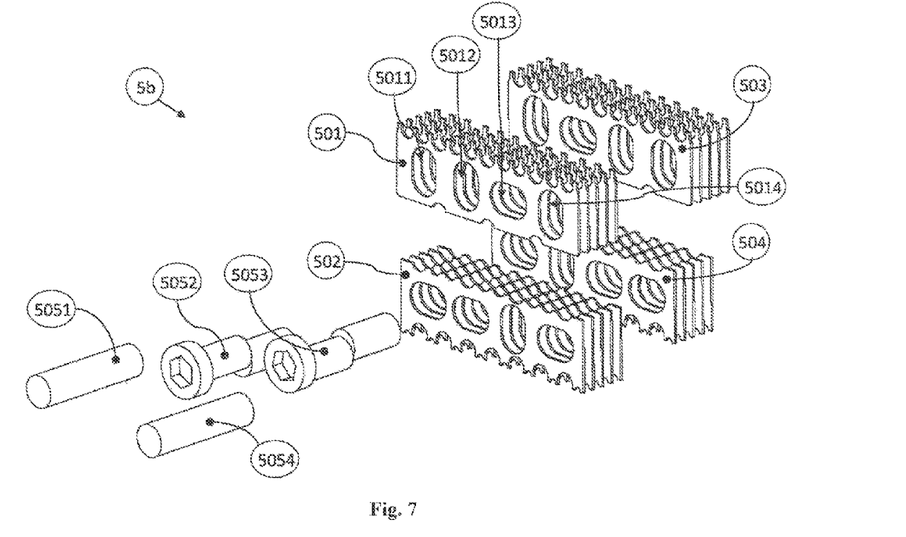
FIG. 7 shows the implant setup that relates to FIG. 6.

FIG. 7 depicts a variant with four different sets of combined plates (501, 502, 503 and 504) that differ in terms of their connection openings (for example, 5011, 5012, 5013 and 5014). The difference can be achieved, for example, by an alternate orientation of the connection openings or the dimensions thereof. Furthermore, the eccentric shafts are represented having two sections, each with a different cranking radius.

Figure 8:
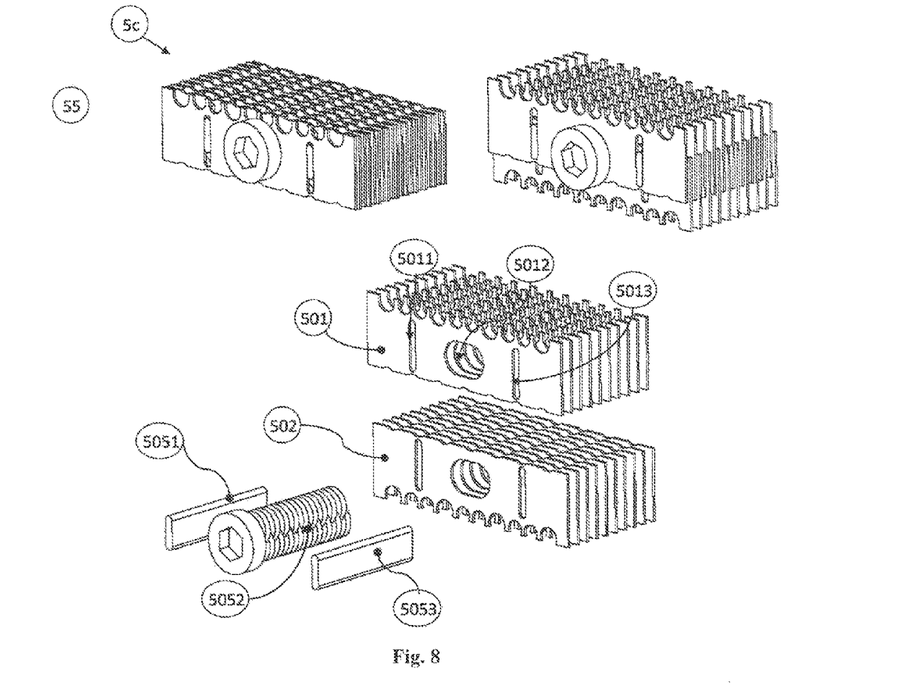
FIG. 8 describes the setup of a further embodied variant.

The embodiment of the height adjustment can, furthermore, be configured such (5c, FIG. 8) that the plates (501 and 502) are identical relative to the cut-outs and in that the eccentric shaft (5052) has a plurality of individual eccentrics having the same or different crank radii. This way, it is possible to achieve different relative movements along the eccentric shaft (5052). To reduce the previously referred to tilting tendency when only a single eccentric shaft is present, it is further possible to use primarily rectangular connection elements (5051 and 5053).

Figure 9:
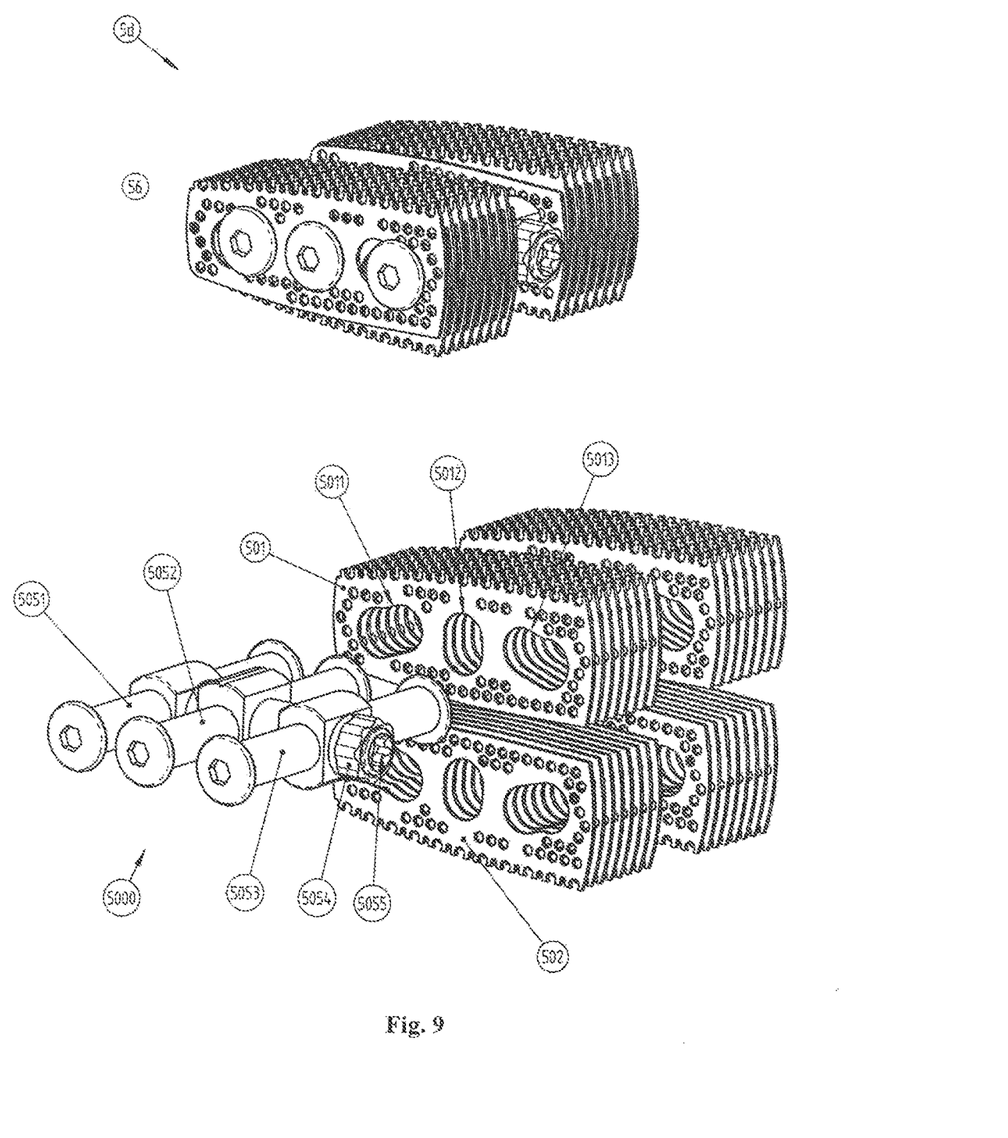
FIG. 9 describes a further embodied variant of the implant as described in FIG. 6.

In a further embodied example (5d, FIG. 9), the adjustment mechanism is embodied by cut-outs (5011, 5013) in the plates (501, 502) and an actuator (5000) engaging therein, wherein the actuator contains at least two axes (5051 and 5053), shafts, bolts, screws, pins, sliding blocks, wedges or similar connection elements, and the distances of which in relation to each other is adjustable. By changing the distances between the axes, the height and the angles of the implant can be changed, wherein the divergence of the correlating cut-outs (5011, 5013) determines, in connection with the change of axis distance, the resulting change in height of the implant. The center axis (5052), as depicted in FIG. 9, serves for supporting and/or fixing the actuator (5000) in place, and it is supported in the center cut-outs (5012) of the plates. The axes can then be adjusted in terms of the distance there-between by an instrument that engages, for example, with a toothed rod with sprocket, a latching or clamping adjustment means or a threaded spindle (5054 or 5055). Further adjustment options are achieved by the use of an electrically or piezoelectrically operated adjustment means or by a length change inside the actuator (5000) that is based on a shape-memory material.

If the contact surfaces are not to be arranged in parallel with the endplates of the vertebrae (or are undefined, respectively) but adjusted at a certain angle, this can be achieved by a simultaneous displacement of both axes in the same direction; for example, by a spindle support having a position that is adjustable by means of a thread relative to the combined plates and/or the enclosing frame. The displacement action of the axes (5051, 5052 and 5053) in relation to each other can be embodied, as shown, using a spindle or other linear drive mechanisms.

Figure 10:
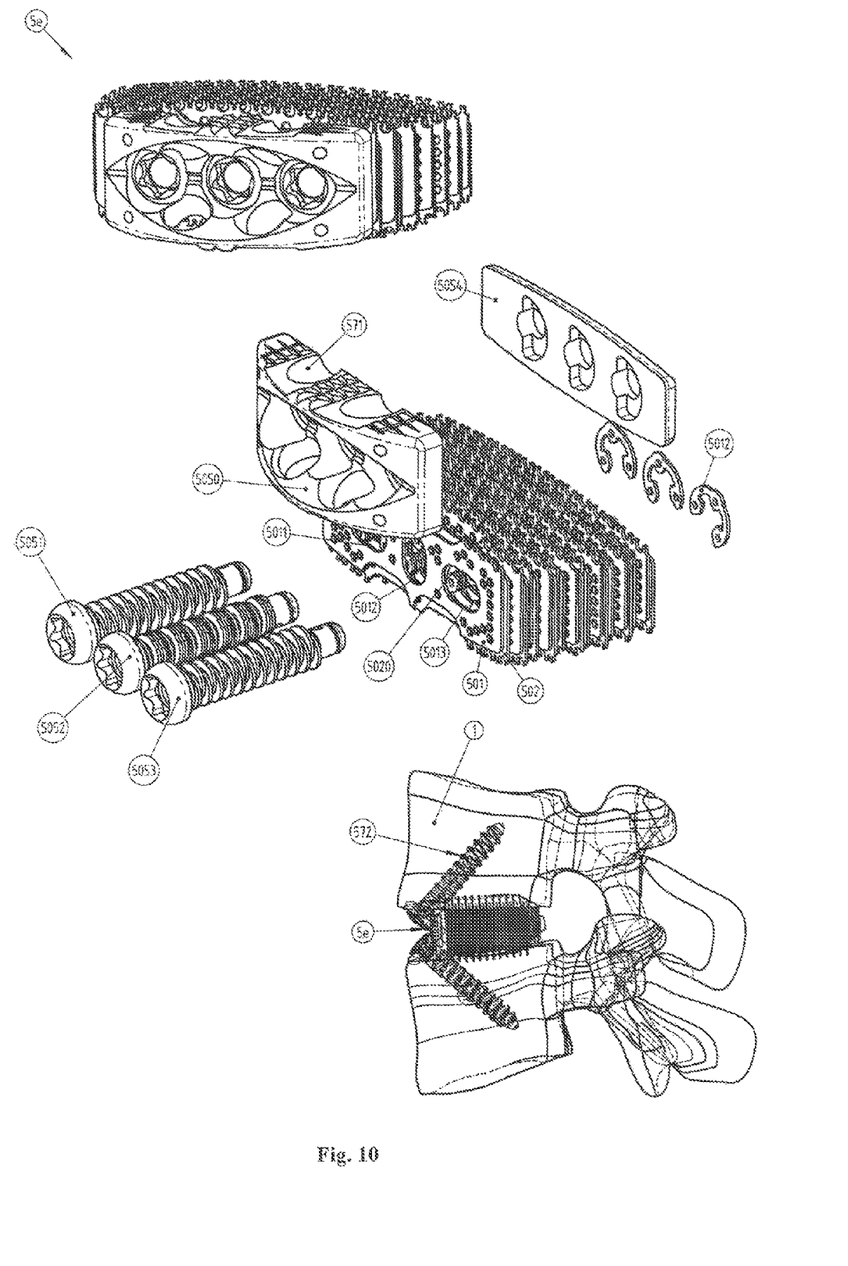
FIG. 10 shows a primary-stable variant of an intervertebral disc implant.

Embodied example (5e) depicts a further version of the intervertebral disc implant (FIG. 10). The variant (5e) is made up of a plurality of plates that are alternately aligned relative to the superior and inferior endplates (501 and 502). One characterizing feature of this embodiment is the combination with a receptacle (5050) that possesses at least one transverse opening (571). Using this opening (571), penetrating bone anchors (572) can be guided into the vertebral body connecting the same to the bone (1). This embodied example (5e) therefore offers an even better level of primary stability. Moreover, embodied example (5e) has three eccentric shafts (5051, 5052 and 5053) that are supported in anterior (5050) and posterior (5054) positions and axially positioned by means of snap rings (5012). Depending on cam shape and cam placement, it is possible to adjust various biomechanically important properties. For example, the embodied example shown here (5e) offers by the selection of the cut-outs (5011, 5012, 5013) the possibility of expanding the implant laterally as well as in terms of height.

Figure 11:
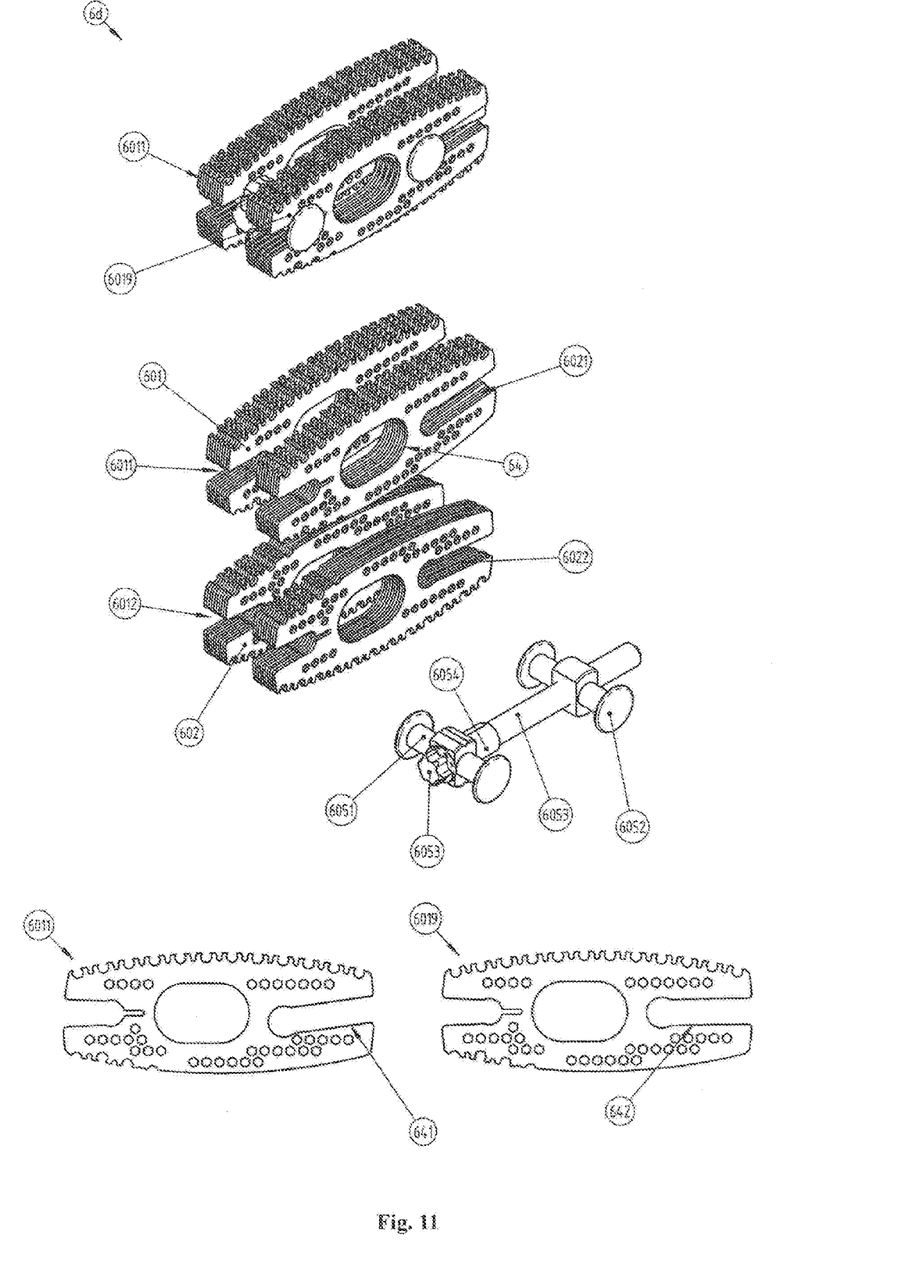
FIG. 11 shows an implant for the posterolateral access and implementation of an uneven height increase over the width of the implant.

Version (6) depicts an embodied example (FIG. 11) that is optimized for posterolateral access. The presently shown implant can have one (or several) cut-outs (64) for the placement of bone graft material. For a better distraction of the intervertebral disc compartment, the anterior erection angle of the implant of the front guide channels (6012, 6022) of the plates (601, 602) can be adjusted from medial to lateral. The angle (642) of the front channel (6021, 6022) therein is changed for each plate, for example from lateral (6011) to medial (6019), such that the height increase has a transverse profile and is thereby optimally adjusted to the geometry of the endplates.

Figure 12:
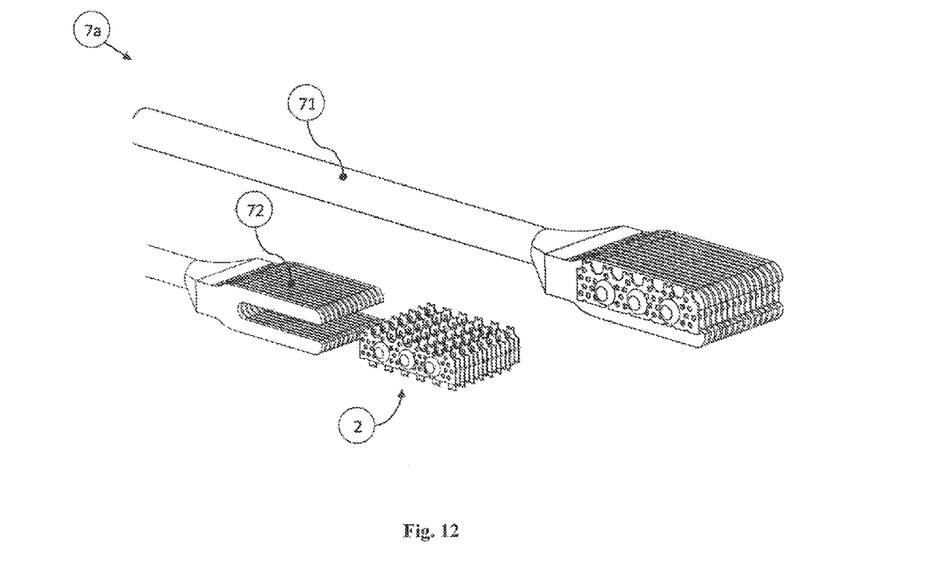
FIG. 12 and FIG. 13 show two exemplary methods of ways for implementing the invention.
Figure 13:
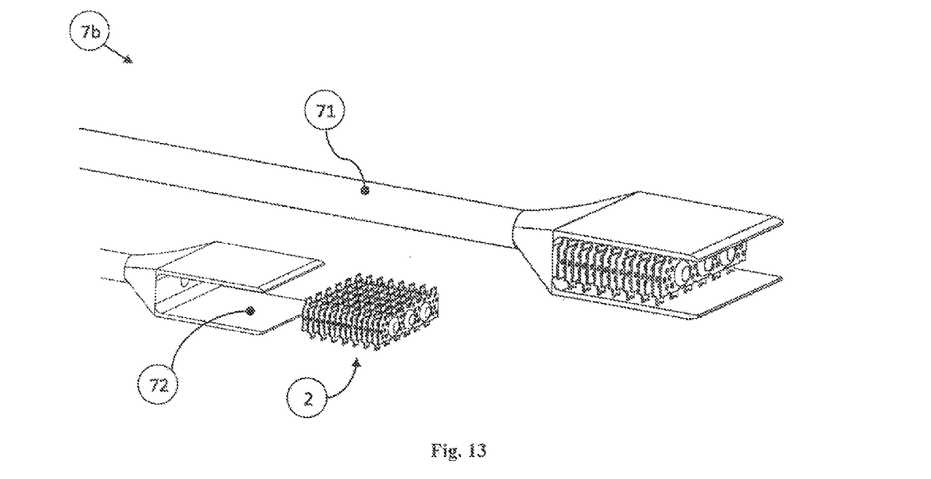

Regarding the implantation of the implant according to the invention (2), two implantation instruments (7a and 7b) are presently shown in an exemplary manner (FIG. 12 and FIG. 13). On the one hand, the instrument (7a) can be configured such that it is made up of a shaft (71) with a distal end (72). The plates of the implant are enveloped by the distal end (72) creating a positive connection, such that the plates with the hook elements are protected by the instrument against inadvertent bending during the insertion and without increasing the height of the implant by the wall strength of the instrument. In the embodiment (7b), an instrument is shown that is intended for another implant that must be inserted in a differently oriented fashion; said instrument fulfills the same preventive functions of embodiment 7a while, however, the overall height during the implantation is minimally increased. Using shaft (71), the implant can be connected to the instrument (for example, by means of a continuous toothed rod), especially in such a manner that the implant is safely held in place and can also be explanted, if necessary.

Figure 14:
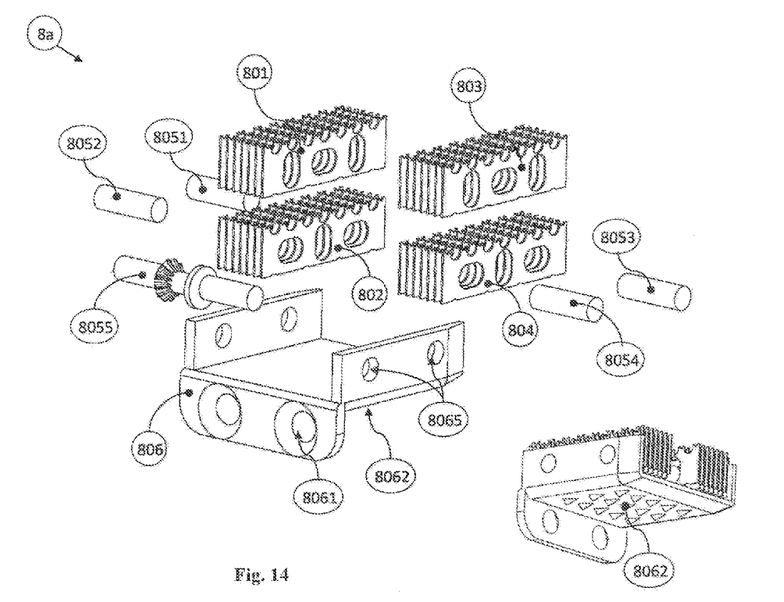
FIG. 14 shows the structural setup of a spine implant according to the invention for resetting a vertebra.
Figure 15:
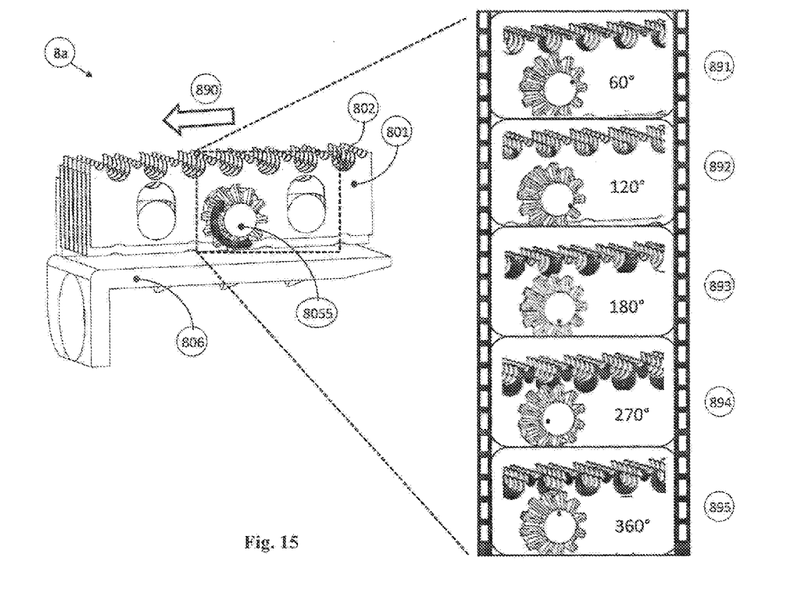
FIG. 15 explains the mechanical implementation of the corrective movement of the implant as shown in FIG. 14.
Figure 16:
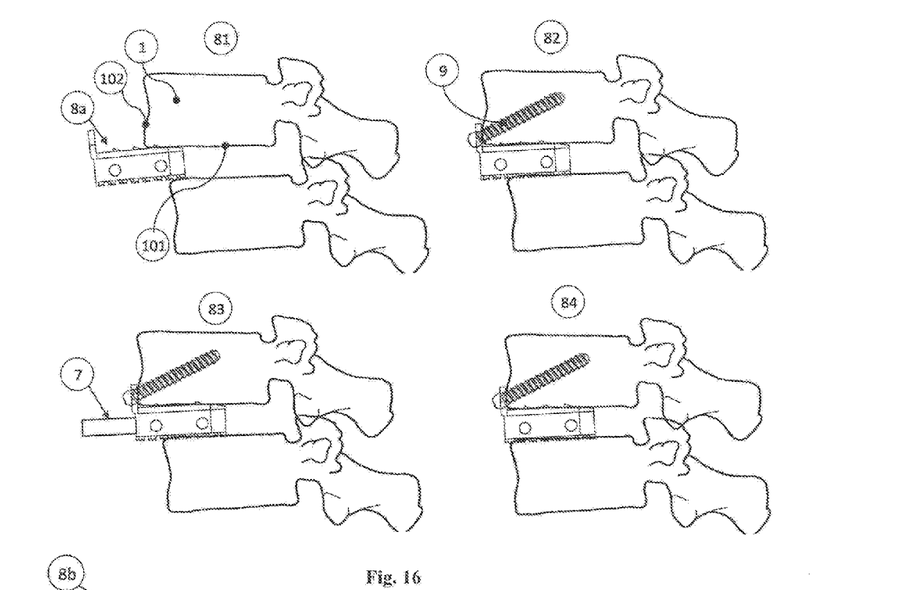

A further embodied example (8a) describes the implementation of a repositioning mechanism of the invention (FIG. 14). The spine implant (8a) is made up of at least one set of combined plates (801, 802, 803 and 804), a holding means (806), various connection elements (8051, 8052, 8053 and 8054) as well as at least one eccentric shaft (8055). The connection elements (8051, 8052, 8053 and 8054) are connected to the holding means (806) at the bearing points (8065). Furthermore, the holding means (806) can possess suitable elements (8062) for anchoring in the endplate. The components are disposed in such a manner that, upon rotation of the eccentric shaft (8055), there occurs a combined lift and translation movement in the combined plates (FIG. 15). For example, it is possible for the rotation (891-895) of the eccentric shaft (8055) to generate peristalsis-type movements between the plates (801 and 802) that result in total in a linear movement or translation (890) on the toothed surface of the implant (8a). Said mechanical translation can be used to reset a misaligned vertebra that is therewith corrected in terms of the AP position. FIG. 16 demonstrates such a resetting process. To this end, the implant (8a) is inserted in the intervertebral space (81). The end with the holding means is fixed in place (82) on the anterior edge of the vertebra (102) therein; this is presently shown in an exemplary manner by a bone screw (9). Subsequently, an instrument (7) is used to transfer (83) a rotational movement to the eccentric shaft (8055). Due to the rotation of the eccentric shaft (8055), the spine implant executes a translation movement (890) on the endplate of the lower vertebra in the AP direction, whereby the vertebra can be positioned and/or the position of the vertebra can be corrected (84).

Figure 17:
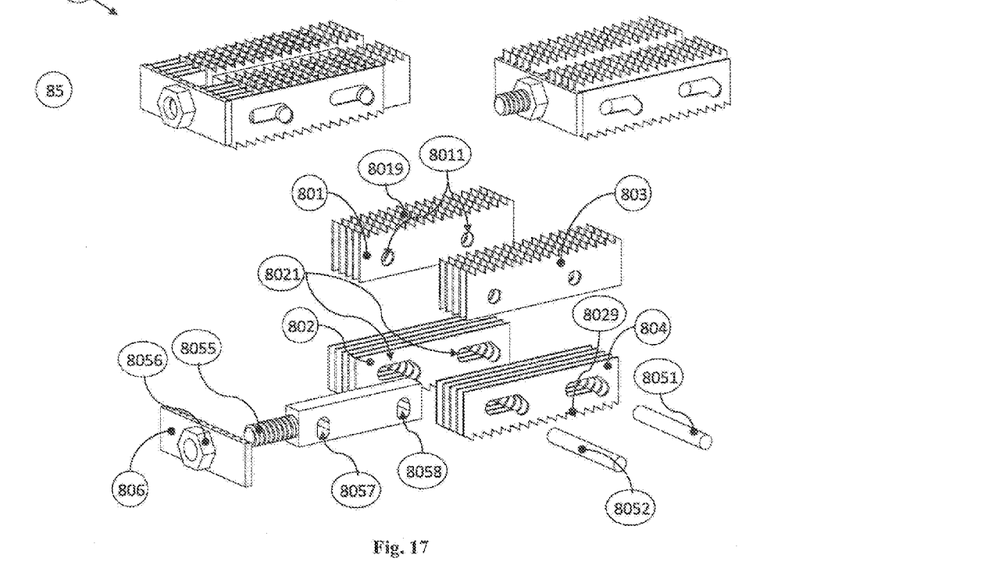
FIG. 17 describes an alternate embodied example relative to the embodied variant as shown in FIG. 14.
Figure 18:
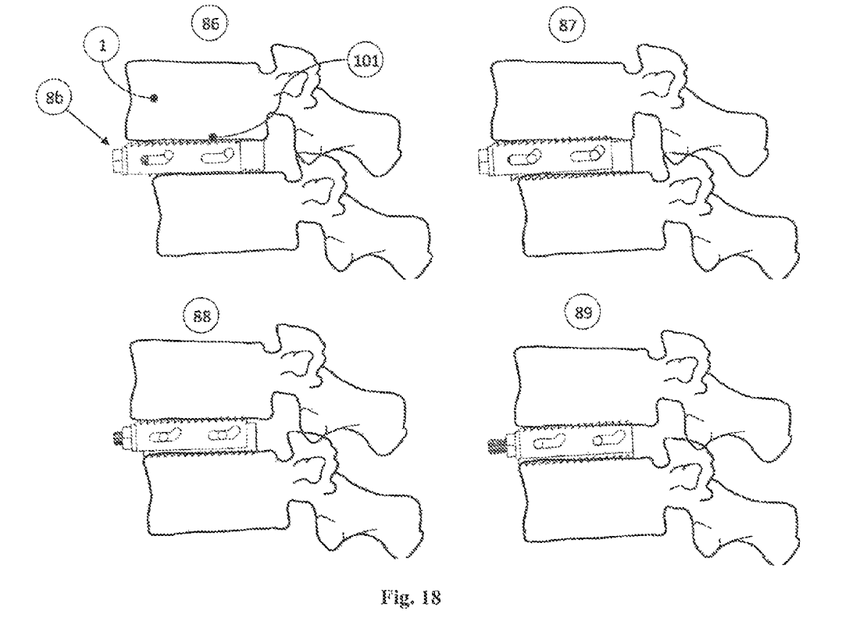
FIG. 18 shows the implantation process of the variant 8b.

A modified embodiment of the repositioning mechanism (8b) of the invention is represented in FIG. 17. The spine implant (8b) includes at least one set of combined plates (801, 802, 803 and 804), a holding means (806), different connection elements (8051, 8052) and at least one spindle (8055). The connection elements (8051, 8052) are connected to the spindle (8055) at the bearing points (8057 and 8058). The spindle (8055) is connected to the frame (806) by a spindle nut (8056). Further, the plates feature profiles in the direction of the bone that are beneficial for anchoring the endplates (101) in the direction of the repositioning (8019 and 8029). The spindle is displaced with the aid of the spindle nut (8056); a part of the combined plates (801 and 803) is thereby transported (85). Based on the course of the bore holes and slots (8011 and 8021) for the bearing shafts (8051 and 8052), it is possible for the implant to be distracted first in terms of height (87) (FIG. 18). After further travel by the spindle, there occurs a translation (88) that provides for a translation and thereby resetting (89).

ABSTRACT

The fusion of two vertebrae is one of the most common procedures in spinal surgery. The invention relates to a spinal implant composed of a plurality of parallel plates. The deliberate introduction of contours in the plates allows for the creation of biomechanically advantageous functions and adjustment options that cannot be provided in any other manner or only at a high cost. The elasticity of the anchoring elements enables the disclosed implant to be adjusted to the osseous endplates, resulting in uniform force distribution and thus prevention of the risk of compaction or endplate compression fracture. The plate structure allows for the use of production methods in which hook-like undercut contours can be created, thus enabling the implant to be superbly anchored in the bone without causing damage thereto. Furthermore, the plates can be interconnected by an actuator in such a way that the height and/or the angular position can be adjusted, thus enabling the intervertebral disk space to be vertically and physically adjusted. The vertical adjustment can vary along the length of the implant such that the segment can also be angularly adjusted. If the plates are interconnected by an eccentric shaft, the combined vertical and translational movement to which the set of plates is subjected can also be used to translationally reposition two vertebrae.

The invention claimed is:

1. A medical implant for placement between bones, particularly between vertebral bodies, comprising a plurality of at least three thin plates, said plates having a material strength that is between 0.02 and 3 mm, and wherein said plates are provided with cut-outs that are suited for colonization by body cells and ossification of said body cells, and wherein said plates are connected by at least one connection element, and wherein said plates are disposed substantially parallel relative to each other at least in one direction, and wherein the distance between the plates is between 0 and 3 mm.

2. The medical implant according to claim 1, wherein the position of the plates can be moved by means of an actuator.

3. The medical implant according to claim 2, wherein the actuator contains at least one eccentric shaft, and wherein the eccentric shaft is defined by a single or a plurality of eccentric pins having identical or different crank radii.

4. The medical implant according to claim 2, wherein the actuator is adjusted by a mechanically operated element selected from the group consisting of a threaded spindle, a toothed rod or a latching and/or clamping mechanism.

5. The medical implant according to claim 2, wherein the actuator is adjusted by an electrically actuated element selected from the group consisting of an electric control drive, electromagnetic control drive or piezoelectric control drive.

6. The medical implant according to claim 2, wherein the actuator contains connection elements selected from the group consisting of bolts, pins, axes, screws, sliding blocks or wedges, and wherein the connection elements are displaceable within the cut-outs or guide channels in the plates.

7. The medical implant according to claim 2, wherein each of the plate cut-outs have a contour, and wherein the actuator comprises an eccentric shaft having eccentric cams, and wherein the contour of the plate cut-outs and the arrangement of the eccentric cams of the eccentric shaft are harmonized such to each other that a rotary movement of the eccentric shaft results in a lift and translation movement of the plates such that for those having the same direction of rotational movement, the translational movement of each of the distracting plates always points in the same direction.

8. The medical implant according to claim 2, having at least two sets of combined plates with cut-outs, an actuator mechanism and connection elements, wherein the cut-outs have a contour adapted for initially distracting a set of combined plates during a displacement of the axes connected to the actuator in relation to a second set of combined plates and to cause, with a further displacement of the axes, a translation movement between the combined plates that is effective in an AP direction.

9. The medical implant according to claim 1, wherein the connection element is embodied as a screw, pin or tube.

10. The medical implant according to claim 1, wherein a distance is defined between the plates by means of rings or discs that are located on the connection elements or by offset embossed patterns or shapes.

11. The medical implant according to claim 1, wherein the connection element is embodied in the design of a strip or a plate, and wherein the connection element has slots, and wherein the distance between the slots defines the distance between the plates.

12. The medical implant according to claim 1, wherein the plates have cut-outs, bars or cut-ins for reducing the rigidity of the implant.

13. The medical implant according to claim 1, wherein the plates contain a toothed structure at faces oriented toward an end surface having a contour that is configured such that there results an undercut.

14. The medical implant according to claim 1, wherein individual plates or all plates have channels grooves or similar indentations that constitute, during assembly of the plates without clearance, at least one channel or at least one capillary.

15. The medical implant according to claim 1, wherein the cut-outs in the plates are semi-permeable, or the implant contains a plurality of bore holes or pores having diameters, respectively, that, owing to their diameters, are suited for cell differentiation or for creating osmotic pressure.

16. The medical implant according to claim 1, wherein the plates are connected to at least one receptacle by means of connection elements or a form closure or closure by adhesive means, and wherein the receptacle is provided with at least one cut-out that is suited to receive a bone anchor.

17. A medical implant for placement between bones, particularly between vertebral bodies, comprising a plurality of at least three thin plates that are disposed substantially in parallel, and wherein the plates are connected to each other by means of at least one connection element, and wherein the position of the plates can be moved relative to each other by means of an actuator,
- wherein the actuator comprises at least one eccentric shaft, the eccentric shaft being defined by a single or a plurality of eccentric pins having identical or different crank radii, and
- wherein the actuator is adjusted by a mechanically or electrically operated element selected from the group consisting of a threaded spindle, a toothed rod, a latching, a clamping mechanism, an electric control drive, electromagnetic control drive or piezoelectric control drive, and
- wherein the actuator comprises connection elements selected from the group consisting of bolts, pins, axes, screws, sliding blocks or wedges, and wherein the connection elements are displaceable within cut-outs or guide channels in the plates, and
- wherein the plates contain a toothed structure at faces oriented toward an end surface having a contour that is configured such that there results an undercut.

18. The medical implant according to claim 17, wherein the connection element is embodied as a screw, pin or tube.

19. The medical implant according to claim 17, wherein the plates have cut-outs, bars or cut-ins for reducing the rigidity of the implant.

20. The medical implant according to claim 19, wherein the cut-outs in the plates are semi-permeable, or the implant contains a plurality of bore holes or pores having diameters, respectively, that, owing to their diameters, are suited for cell differentiation or for creating osmotic pressure.

21. The medical implant according to claim 17, wherein individual plates or all plates have channels grooves or similar indentations that constitute, during assembly of the plates without clearance, at least one channel or at least one capillary.

22. The medical implant according to claim 17, wherein the plates are connected to at least one receptacle by means of connection elements or a form closure or closure by adhesive means, and wherein the receptacle is provided with at least one cut-out that is suited to receive a bone anchor.

23. A medical implant for placement between bones, particularly between vertebral bodies, comprising a plurality of at least three thin plates that are disposed substantially in parallel, and wherein the plates are connected to each other by means of at least one connection element, and wherein the position of the plates can be moved by means of an actuator,
- wherein each of the plates comprises at least one cut-out having a contour, and wherein the actuator comprises an eccentric shaft having eccentric cams, and wherein the contour of the plate cut-outs and the arrangement of the eccentric cams of the eccentric shaft are harmonized such to each other that a rotary movement of the eccentric shaft results in a lift and translation movement of the plates such that for those having the same direction of rotational movement, the translational movement of each of the distracting plates always points in the same direction.

* * * * *